United States Patent
Mueller

(10) Patent No.: US 9,659,152 B2
(45) Date of Patent: May 23, 2017

(54) COMPUTER-IMPLEMENTED TECHNIQUE FOR DEFINING A BONE CUT

(71) Applicant: CADFEM GmbH, Grafing b. Munchen (DE)

(72) Inventor: Christoph Mueller, Munich (DE)

(73) Assignee: STRYKER EUROPEAN HOLDINGS I, LLC

( * ) Notice: Subject to any disclaimer, the term of this patent is extended or adjusted under 35 U.S.C. 154(b) by 486 days.

(21) Appl. No.: 14/249,695

(22) Filed: Apr. 10, 2014

(65) Prior Publication Data
US 2014/0343557 A1 Nov. 20, 2014

(30) Foreign Application Priority Data
Apr. 12, 2013 (EP) ..................................... 13001916

(51) Int. Cl.
*A61B 19/00* (2006.01)
*G06F 19/00* (2011.01)
(Continued)

(52) U.S. Cl.
CPC .......... *G06F 19/3437* (2013.01); *A61B 34/10* (2016.02); *A61B 34/20* (2016.02); *A61B 2034/105* (2016.02); *A61B 2034/107* (2016.02)

(58) Field of Classification Search
CPC .............. A61B 34/10; A61B 2034/101; A61B 2034/105; A61B 2034/107; A61B 17/176; G06F 19/34; G06F 19/3437
See application file for complete search history.

(56) References Cited

U.S. PATENT DOCUMENTS 6,254,639 B1 * 7/2001 Peckitt ................... A61B 17/80
                                                    623/11.11
6,309,220 B1 * 10/2001 Gittleman ............ A61B 17/176
                                                    433/173
(Continued)

FOREIGN PATENT DOCUMENTS

EP    1726265 A1   11/2006
WO    2006000063 A1   1/2006
WO    2012139999 A1   10/2012

OTHER PUBLICATIONS

European Search Report for Application No. 13001916.9 dated Sep. 20, 2013.

*Primary Examiner* — Christian Sevilla
*Assistant Examiner* — Eric S Gibson
(74) *Attorney, Agent, or Firm* — Belles Katz LLC

(57) ABSTRACT

A technique for generating a data set that geometrically defines a bone cut configuration for transverse maxillary distraction is using a computer-implemented method. An aspect of the technique comprises creating a numeric model of a maxilla based on patient-specific data of the maxilla. The numeric model is representative of mechanical properties of the maxilla. Based on the numeric model thus generated, one or more cut configurations for one or more bone cuts on at least one of a left hand side and a right hand side of the maxilla are determined. Each cut configuration has been determined to compensate for asymmetric mechanical properties of the maxilla. In a further step, a data set indicative of the one or more cut configurations thus determined is generated. The data set may be used to create a surgical template or jig, for computer-assisted surgery or a surgical navigation system.

22 Claims, 14 Drawing Sheets

(51) Int. Cl.
*A61B 34/20* (2016.01)
*A61B 34/10* (2016.01)

(56) References Cited

U.S. PATENT DOCUMENTS

| | | | |
|---|---|---|---|
| 7,322,987 B2 | 1/2008 | Schendel | |
| 7,892,241 B2 | 2/2011 | Ahmad et al. | |
| 7,909,610 B1 * | 3/2011 | Amato | G09B 23/32 |
| | | | 434/270 |
| 7,953,260 B2 * | 5/2011 | Weinzweig | G06F 19/3437 |
| | | | 382/128 |
| 8,260,018 B2 | 9/2012 | Lang et al. | |
| 8,535,063 B1 * | 9/2013 | Amato | G09B 23/32 |
| | | | 434/270 |
| 2003/0097137 A1 * | 5/2003 | Schendel | A61B 17/663 |
| | | | 606/105 |
| 2004/0068187 A1 * | 4/2004 | Krause | A61B 17/15 |
| | | | 600/443 |
| 2004/0117015 A1 * | 6/2004 | Biscup | A61F 2/30942 |
| | | | 623/16.11 |
| 2005/0039759 A1 * | 2/2005 | Mauro | A61C 11/00 |
| | | | 128/859 |
| 2010/0152741 A1 * | 6/2010 | Park | A61B 17/155 |
| | | | 606/89 |
| 2011/0060558 A1 * | 3/2011 | Pettersson | A61B 17/8685 |
| | | | 703/1 |
| 2011/0269100 A1 * | 11/2011 | Furrer | A61B 17/151 |
| | | | 433/72 |
| 2012/0029574 A1 * | 2/2012 | Furrer | A61B 17/151 |
| | | | 606/280 |
| 2012/0063655 A1 * | 3/2012 | Dean | G06F 19/321 |
| | | | 382/128 |
| 2012/0230566 A1 * | 9/2012 | Dean | G06T 19/00 |
| | | | 382/131 |
| 2014/0149095 A1 * | 5/2014 | Davison | A61B 17/1739 |
| | | | 703/7 |
| 2014/0343557 A1 * | 11/2014 | Mueller | A61B 19/50 |
| | | | 606/87 |
| 2015/0272598 A1 * | 10/2015 | Dubois | A61B 34/10 |
| | | | 606/280 |
| 2016/0135890 A1 * | 5/2016 | Cattin | A61B 34/10 |
| | | | 606/11 |
| 2016/0235487 A1 * | 8/2016 | Davison | A61B 17/1739 |
| 2016/0331427 A1 * | 11/2016 | Waizenegger | A61B 17/176 |

* cited by examiner

| 1 | F1_F2_Symmetry | ReactionForce1_X−ReactionForce2_X |
|---|---|---|
| 2 | F1_F2_Reduction | ReactionForce1_X+ReactionForce2_X |
| 3 | Christa_length_left | LeftChrista_R+LeftChrista_F |
| 4 | Christa_length_right | RightChrista_R+RightChrista_F |
| 5 | Objectives | (5*)F1_F2_symmetry+(6*)F1_F2_Reduction+(*)Christa_Length_left+(1*)Christa_lenth_right |

Weighting factor

| Design 1 | Design 47 | Design 77 |
|---|---|---|
| Reaction Force = 2539.81N<br>Symmetry = 145.768<br>Min. cut length | Reaction Force = 2272.99N<br>Symmetry = 5.3224<br>Max. cut length | Reaction force=2237.49N<br>Symmetry=0.3612<br>Optimum. cut length |

COMPUTER-IMPLEMENTED TECHNIQUE FOR DEFINING A BONE CUT

CROSS-REFERENCE TO RELATED APPLICATIONS

This application claims priority to European Patent Application No. 13001916.9 filed Apr. 12, 2013, the disclosure of which is incorporated herein by reference.

BACKGROUND OF THE INVENTION

The present disclosure generally relates to the field of providing computer-implemented assistance to surgeons. In particular, a technique that enables a computer-implemented definition of a bone cut configuration is provided. The technique may be implemented in the form of a method, device or computer-program product. The computer-implemented technique generates a data set that geometrically defines the bone cut configuration.

Transverse maxillary deficiencies can be treated by intraoral skeletal correction. To this end, in a first step bone cuts are performed in midpalatal and pterygoid regions of the maxilla to separate left and right hand portions of the maxilla. In a next step, an intraoral distraction device is implanted that locally acts on the left and right hand portions of the maxilla so as to move them apart in a transverse direction. This distraction is performed in multiple steps over an extended period of time.

US 2003/0097137A teaches an exemplary distraction device suitable for horizontal, vertical and transverse maxillary distraction. The distraction device comprises a facebow formed from multiple sections attachable to the maxilla. Each pair of adjacent sections is joined via a threaded link. The threaded link can be rotated so as to move the two sections apart from each other and thus cause distraction. There exist, of course, various alternative devices for transverse maxillary distraction.

It has empirically been found that transverse maxillary distraction often leads to an asymmetric correction of the maxillary deficiency. The asymmetric distraction can in part be attributed to local variations of maxillary bone stiffness. For example, such stiffness variations may cause the displacement of the left hand side of the maxilla relative to the midpalatal bone cut to differ from the displacement of the right hand side of the maxilla relative to that bone cut. Depending on the specific amount the displacements differ, a non-pleasing aesthetical result may be obtained.

BRIEF SUMMARY OF THE INVENTION

It is an aspect of the present disclosure to provide a computer-implemented technique that helps a surgeon to combat an undesired skeletal asymmetry as a result of transverse maxillary distraction.

According to one aspect, a computer-implemented method of generating a data set that geometrically defines at least one bone cut configuration for transverse maxillary distraction is provided, wherein the method comprises creating, based on patient-specific data of the maxilla, a numeric model representative of mechanic properties of the maxilla, determining, based on the numeric model thus generated, one or more cut configurations for one or more first bone cuts on at least one of a left hand side and a right hand side of the maxilla, wherein the one or more cut configurations are determined to compensate for asymmetric mechanic properties of the maxilla upon distraction, and generating a data set indicative of the at least one cut configuration.

It will be appreciated that the expressions "left" and "right" as used herein can be used interchangeably and only denote two opposite sides of the maxilla in a transverse direction. It will further be appreciated that the numeric model may be any mathematical model expressing the mechanic properties of the maxilla in numbers.

The one or more first bone cuts derived from the numeric model may locally weaken the maxilla. Such a local weakening can be calculated based on the numeric model so as to compensate for the asymmetric mechanic properties of the maxilla for the purpose of symmetric transverse maxillary distraction. As an example, the one or more first bone cuts may be defined to partially or fully extend in a lateral midfacial area (e.g., in a lateral sinus wall). The asymmetric mechanic properties of the maxilla may thus be compensated for by intentionally weakening the lateral midfacial area (e.g., the lateral sinus wall). In certain implementations, one or more first bone cuts in alternative or additional regions may be provided.

Each cut configuration may comprise geometric data indicative of the associated first bone cut. As an example, each cut configuration may comprise data indicative of one or more of a cutting plane, a (e.g., curved) cutting line, a cutting direction, a cutting length and one or more (e.g., two) bone cut boundary points. Those data may be provided in a coordinate system of the numeric model or in any other coordinate system. As an example, the data may be provided in a first coordinate system (e.g., of the numeric model) and later on be transformed in a second coordinate system (e.g., of a patient during surgery) depending on the specific use of the data.

Determining the one or more cut configurations may comprise introducing the one or more first bone cuts in the numeric model of the maxilla. The resulting numeric model may then be analysed as to its mechanic properties upon distraction (e.g., in terms of a reaction force resulting from applying a certain displacement in the numeric model or in terms of a displacement resulting from applying a certain distraction force in the numeric model).

Determining the one or more cut configurations may additionally, or as an alternative, comprise introducing one or more second bone cuts in the numeric model of the maxilla. The one or more second bone cuts may at least partially separate in the numeric model regions moved apart upon distraction from regions essentially not affected by distraction. The resulting numeric model may then be analysed as to its mechanic properties upon distraction. The one or more second bone cuts may be introduced in at least one of a pterygoid region and a palatine region of the maxilla.

The patient-specific data may be provided in the form of voxel-based data, pixel-based data or any other data type. Creating the numeric model may comprise processing the patient-specific (e.g., voxel-based) data to determine at least one of contour data and stiffness data for the maxilla, and calculating the numeric model from at least one of the contour data and the stiffness data.

The numeric model may be indicative of one or more of a stiffness of the maxilla, a reaction force upon distraction of the maxilla and a displacement upon distraction of the maxilla. The numeric model may be processed to calculate any of these items for determining the one or more cut configurations.

The one or more cut configurations may generally be determined so as to balance asymmetric mechanic properties of the maxilla. Such asymmetric mechanic properties may be reflected in at least one of a stiffness asymmetry of the maxilla, asymmetric reaction forces upon distraction and asymmetric displacements upon distraction. As an example, for a given displacement the amount of the resulting reaction force on the left hand side of the maxilla may differ from the amount of the resulting opposite reaction force on the right hand side of the maxilla. As another example, for a given distraction force amount the displacement on the left hand side of the maxilla may differ from the opposite displacement on the right hand side of the maxilla. Such asymmetries may be derived based on the numeric model.

In one implementation, determining the one or more cut configurations comprises applying a predetermined distraction force on each of a first side and a second side of the numeric model that correspond to the left hand side and the right hand side of the maxilla, respectively, and determining the resulting displacements of the first side and the second side of the numeric model, respectively. In another configuration, determining the one or more cut configurations comprises applying a predetermined displacement on each of the first side and the second side of the numeric model and determining the reaction forces on the first side and the second side of the numeric model, respectively, associated with the displacements. Both implementations could, of course, be combined as needed.

The distraction forces or displacements may generally be applied in at least one of a region of the (e.g., first) molars and a region of the canines. The distraction forces or displacements may be applied in additional or alternative regions. The specific application points of force vectors or displacement vectors may generally be selected based on the configuration of the distraction device and its application to the maxilla.

According to a first variant, determining the one or more cut configurations based on the numeric model comprises applying an iterative calculation procedure based on one or more optimization parameters. In each iteration, at least one new cut configuration may be calculated, and a new numeric model may be created based thereon for the next iteration. The one or more optimization parameters may include at least one of a minimum cut length (e.g., on a cut-by-cut basis or as an accumulated cut length), equalization of stiffnesses on a first side and a second side of the numeric model that correspond to the left hand side and the right hand side of the maxilla, respectively, equalization of displacements on the first side and the second side, equalization of distraction or reaction forces on the first side and the second side, and minimum distraction or reaction forces.

According to an alternative variant, initially multiple cut configurations are defined for which associated numeric models are determined and analyzed as to one or more quality parameters. Based on the analysis, one or more of the initially defined cut configurations may then be selected for generating the data set. The one or more quality parameters may include at least one of a minimum cut length (e.g., on a cut-by-cut basis or as an accumulated cut length), equalization of stiffnesses on a first side and a second side of the numeric model that correspond to the left hand side and the right hand side of the maxilla, respectively, equalization of displacements on the first side and the second side, equalization of distraction or reaction forces on the first side and the second side, and minimum distraction or reaction forces.

Further provided is a computer product comprising program code portions for performing the steps of any of the methods and method aspects presented herein when the computer program product is executed on a computing device or a set of interconnected computing devices. The computer program product may be stored on one or more computer-readable recording mediums.

The data set generated according to the method implementation presented therein may be used for various purposes. As a first example, the data set may be used (e.g. by a rapid prototyping device or a programmable machining device) for manufacturing the surgical template or jig for bone cutting. In such a case, the data set may have a format compliant with Computer Aided Design (CAD) or Computer Aided Manufacturing (CAM). As an example, the data set may be generated in a Stereolitography (STL) format. The template or jig may be applied to the patient's maxilla so as to assist the bone cutting operation.

In a second example, the data set may be used for controlling a computer-assisted surgery system for bone cutting. In other words, the data set may comprise control information for automatically or semi-automatically (e.g., under the supervision or control of a surgeon) performing a bone cutting procedure. The computer-assisted surgery system may comprise a robot arm or any other robotic features and a surgical tool (e.g., a bone saw).

As a still further example, a surgical navigation system may be controlled based on the data set for bone cutting. In such a case the data set may comprise control information for providing visual, tactile or acoustic guidance to a surgeon. The navigation system may, for example, track the position of a surgical tool (e.g., a bone saw) relative to the patient and visualize that position (e.g., relative to a representation of one or more target cut configurations derived from the data set) on the display device.

Thus, also provided is a surgical template or jig for bone cutting that has been manufactured on the basis of the data set. Still further, a computer-assisted surgery system as well as a surgical navigation system controlled on the basis of the data set are provided.

According to a further aspect, a computing device for generating a data set that geometrically defines at least one bone cut configuration for transverse maxillary distraction is provided, wherein the device comprising a processor configured by a computer program to create, based on patient-specific data of the maxilla, a numeric model representative of mechanic properties of the maxilla, to determine, based on the numeric model thus generated, one or more cut configurations for one or more bone cuts on at least of a left hand side and a right hand side of the maxilla, wherein the one or more cut configurations are determined to compensate for asymmetric mechanic properties of the maxilla upon distraction, and to generate a data set indicative of the at least one cut configuration.

According to a still further aspect of the present disclosure, a data set or a data signal comprising the data set that geometrically defines the one or more cut configurations is provided, wherein the data set has been generated as discussed herein.

BRIEF DESCRIPTION OF THE DRAWINGS

Further aspects, details and advantages of the present disclosure will become apparent from the following description of exemplary embodiments in conjunction with the accompanying drawings, wherein:

FIG. 9 is an exemplary table illustrating derivation of an optimization criterion based on a plurality of optimization parameters;

FIG. 11 is a schematic diagram further illustrating the optimization procedure of FIG. 10;

DETAILED DESCRIPTION

In the following description of exemplary embodiments, for purposes of explanation and not limitation, specific details are set forth, such as particular methods, functions and procedures, in order to provide a thorough understanding of the technique presented herein. It will be apparent to one skilled in the art that this technique may be practiced in other embodiments that depart from these specific details. For example, while the following embodiments will primarily be described on the basis of an FEM implementation, it will be evident that the technique presented therein could also be implemented using meshless numeric models.

Moreover, those skilled in the art will appreciate that the methods, functions and steps explained herein may be implemented using software functioning in conjunction with a programmed microprocessor, an Application Specific Integrated Circuit (ASIC), a Digital Signal Processor (DSP) or a general purpose computer. It will also be appreciated that while the following embodiments will primarily be described in the context of methods and devices, the present disclosure may also be embodied in a computer program product which can be loaded to run on a computer or a distributed computer system comprising one or more processors and one or more memories functioning as storage, wherein the one or more memories are configured to store one or more programs that may perform the methods, functions and steps disclosed herein.

Figure 1:
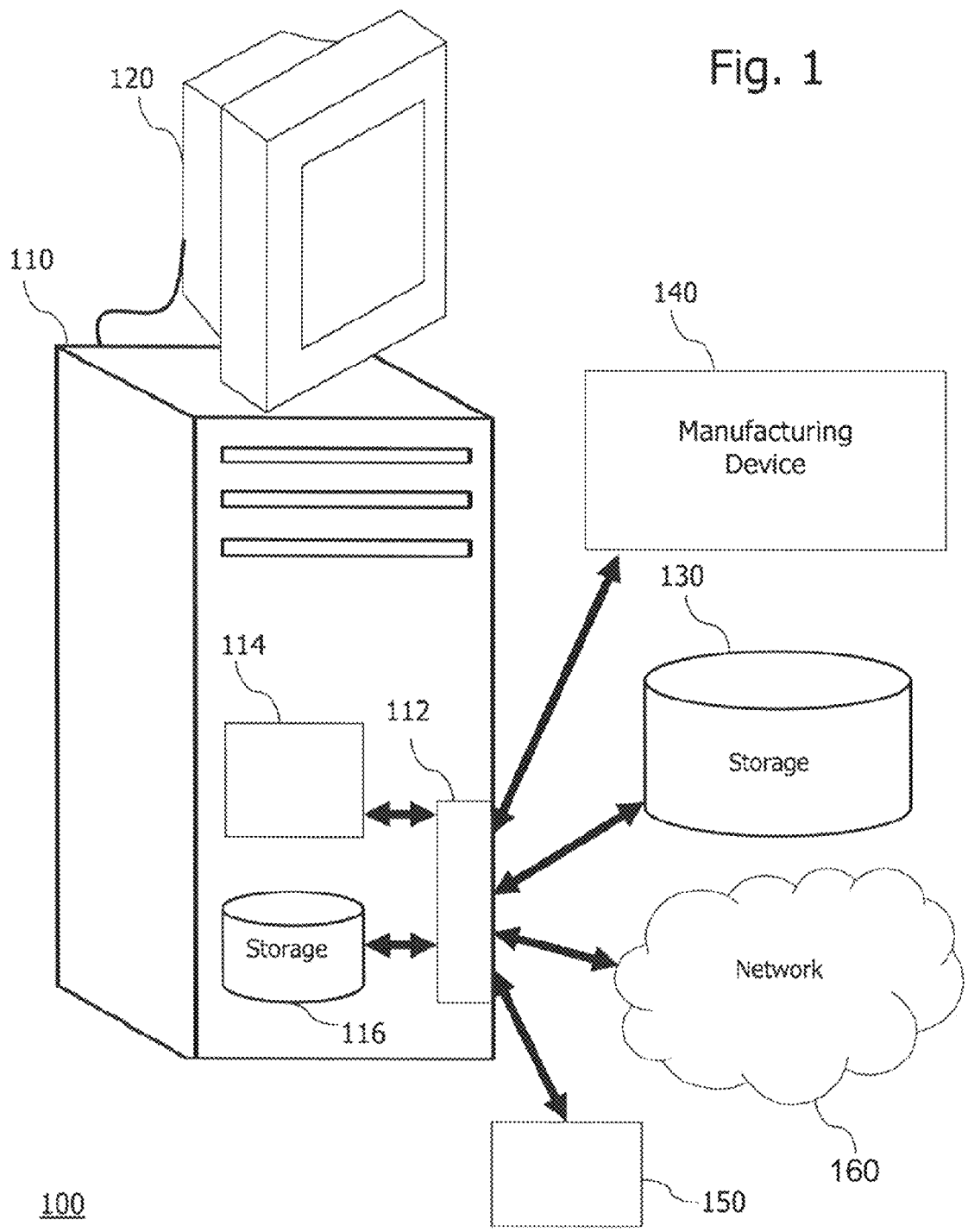
FIG. 1 schematically illustrates an embodiment of a system for generating a data set that geometrically defines a bone cut configuration for transverse maxillary distraction.

FIG. 1 illustrates an embodiment of a system 100 for generating data sets that geometrically define one or more bone cut configurations. As illustrated in FIG. 1, the system 100 comprises a computing device 110 (such as a personal or laptop computer), a display device 120 (such as a computer monitor), and an external storage 130 (such as hard disk or a semiconductor memory in which a data base is provided) for storing the generated data sets. The system 100 also includes a manufacturing device 140 such as a rapid prototyping device or any programmable machining device.

As shown in FIG. 1, the system 100 further comprises at least one user-operable input device 150 (such as a keyboard, a mouse or a trackball) for generating or triggering the generation of user interaction signals. In one implementation, the display device 120 and the input device 150 may be integrated into a touchscreen.

The computing device 110 comprises an interface 112, at least one processor 114 (such as a Central Processing Unit, CPU) and an internal storage 116 (such as a hard disk or a semiconductor memory) for storing program code and, optionally, the generated data sets. The interface 112 is configured as an input/output interface for establishing a communication between the computing device 110 on the one hand and, on the other hand, the display device 120, the storage 130, the manufacturing device 140, the input device 150 and a computer network 160 (such as a Local Area Network, LAN, and/or the Internet). The interface 112 can be realized in the form of one or more hardware components, one or more software components or a combination of one or more hardware components and one or more software components.

The system 100 of FIG. 1 may further comprise one or both of a computer-assisted surgery system and a surgical navigation system (not shown). Those systems may be attached to the computing device 110 via the network 160. They may also have access to the data sets in the external storage 130.

In the following, exemplary modes of operation of the system 100 illustrated in FIG. 1 will be discussed in more detail with reference to the remaining drawings. It should be noted that the operational procedures discussed herein could also be implemented in a system having a configuration different from that shown in FIG. 1.

The system 100 is generally operated to generate a data set that geometrically defines a bone cut configuration for transverse maxillary distraction. As mentioned initially, conventional approaches for transverse maxillary distraction may result in an asymmetric correction of the maxillary deficiency, which is often not acceptable from an aesthetic standpoint. For this reason the embodiments presented hereinafter provide computer-implemented assistance to a surgeon to compensate for asymmetric mechanic properties of the maxilla upon distraction.

Figure 2A:
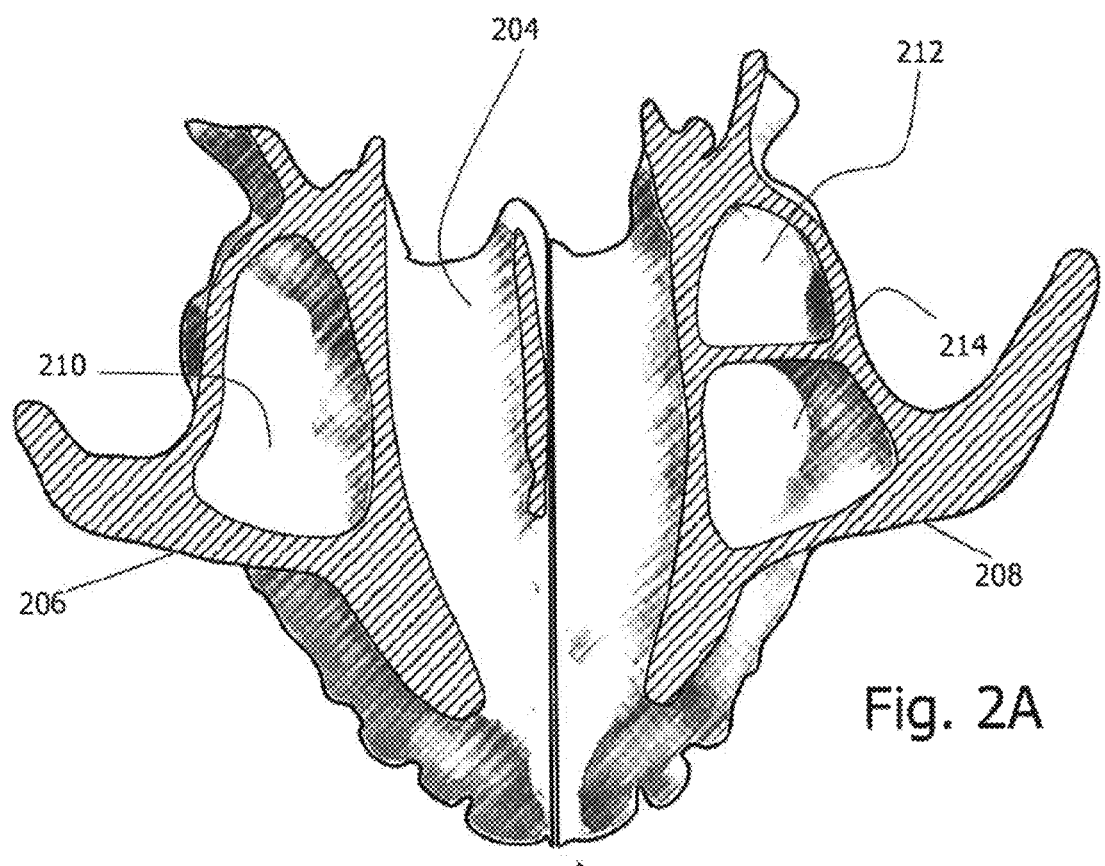
FIG. 2A, 2B schematically illustrate a cross-section of a patient's maxilla and a transverse distraction procedure applied to that maxilla.

FIG. 2A illustrates a cross-sectional topview of a patient's maxilla 200. The maxilla 200 comprises a left hand side 206 and a right hand side 208 separated by a standard bone cut 202. It will be appreciated that the expressions "left" and "right" only denote two opposite sides of the maxilla 200 in a transverse direction. The aim of transverse maxillary distraction is to move regions of the two sides 206, 208 apart from each other to compensate for transverse maxillary deficiencies.

FIG. 2A also visualizes an exemplary standard bone cut 202 performed in a midpalatal region 204 of the maxilla 200. Further standard bone cuts (not shown) are performed in pterygoid regions of the maxilla 200. The standard bone cuts separate regions of the maxilla 200 that will be moved apart upon distraction from regions essentially not effected by distraction. Depending on the anatomic situation and surgical needs, one or more (or all) of those standard bone cuts could be omitted, or further standard bone cuts could be added.

Figure 2B:
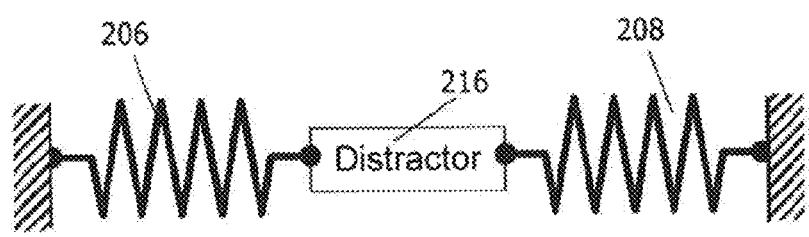

As becomes apparent from FIG. 2A, the configurations of the bony structures on the left hand side 206 and the right hand side 208 of the maxilla 200 differ substantially. For example, while the left hand side 206 only comprises a single chamber 210, two such chambers 212, 214 are provided on the right hand side 208. These skeletal differences result in asymmetric stiffnesses of the left hand side 206 and right hand side 208 of the maxilla 200. Consequently, when placing a transverse distractor device 216 between regions of the left hand side 206 and the right hand side 208 of the maxilla 200 across the bone cut 202 as illustrated in FIG. 2B and applying a predefined distraction force therebetween, the stiffer right hand side 208 of the maxilla 200 will be displaced less relative to the bone cut 202 than the opposite left hand side 206. The (different) stiffnesses of the left-hand side 206 and the right hand side 208 of the maxilla are represented in FIG. 2B in the form of springs with (different) spring constants.

Figure 3:
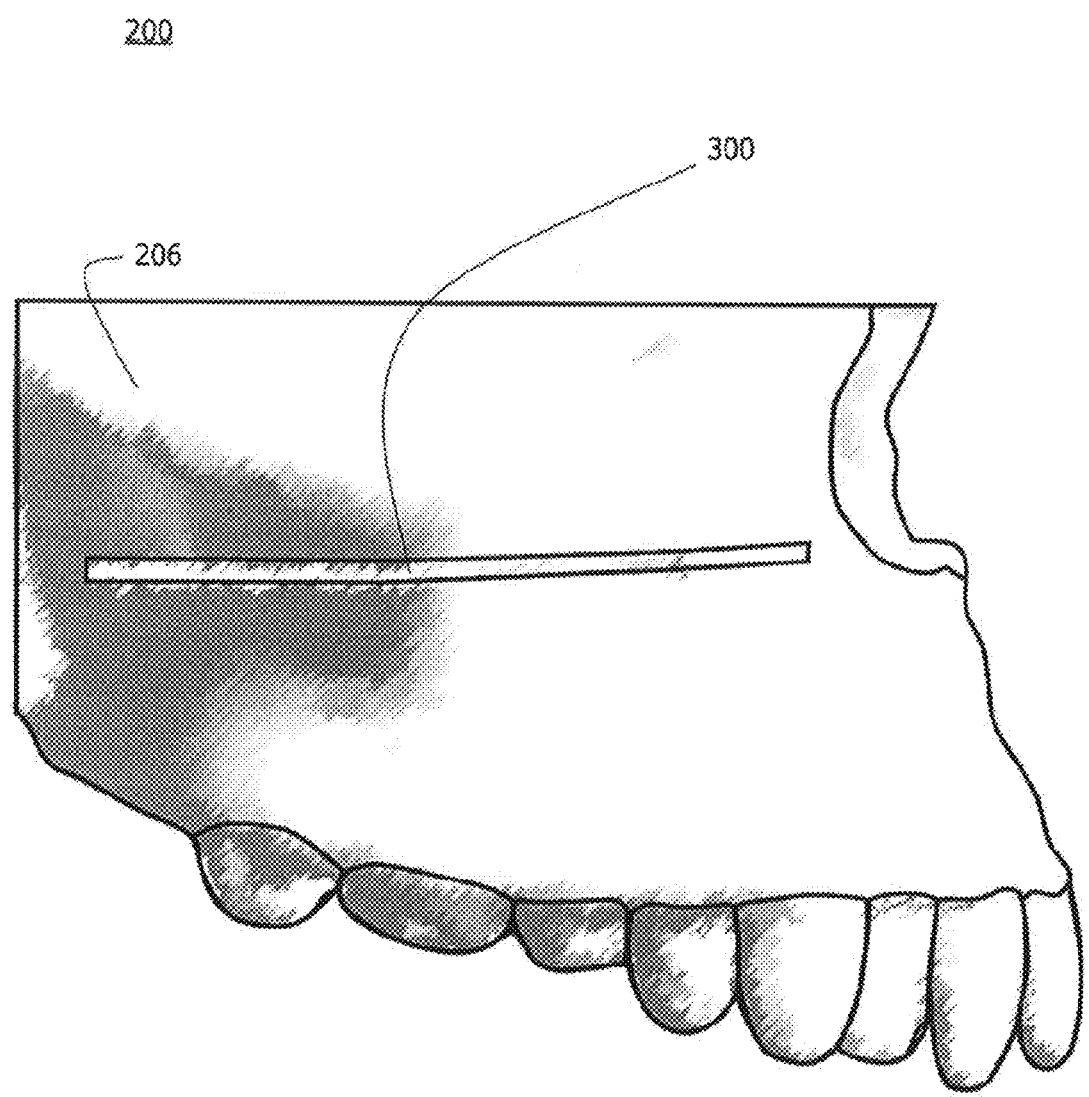
FIG. 3 is a schematic diagram illustrating an exemplary bone cut as provided in a facies infratemporalis region of the maxilla.

The resulting asymmetric displacements relative to the bone cut 202 lead to an asymmetric correction of the maxillary deficiency, and this asymmetry it is to be tackled by the computer-implemented technique presented herein. Specifically, it has been recognized that the asymmetric mechanic properties of the maxilla 200 discussed with reference to FIG. 2A can be compensated for by providing one or more bone cuts 300 as illustrated in FIG. 3. The one or more bone cuts 300 are provided in addition to the one or more optional standard bone cuts (such as bone cut 202 of FIG. 2) conventionally used in connection with transverse maxillary distraction.

A bone cut 300 as illustrated in FIG. 3 may be provided on one or both of the left hand side 206 and the right hand side 208 of the maxilla 200. Moreover, it would also be possible to provide more than one such bone cut 300 in each of the left hand side 206 and the right hand side side 208 of the maxilla 200. In the present embodiment the at least one bone cut 300 is provided in a lateral midface area of the maxilla 200 and, specifically, in the lateral sinus wall. The associated lateral midface area of the maxilla 200 is thus locally weakened. The local weakening is tailored to the stiffness asymmetry of the maxilla 200 and results in the desired symmetric distraction. The cut configuration underlying each bone cut 300 is determined in a computer-implemented manner using the system 100 of FIG. 1.

Figure 4:
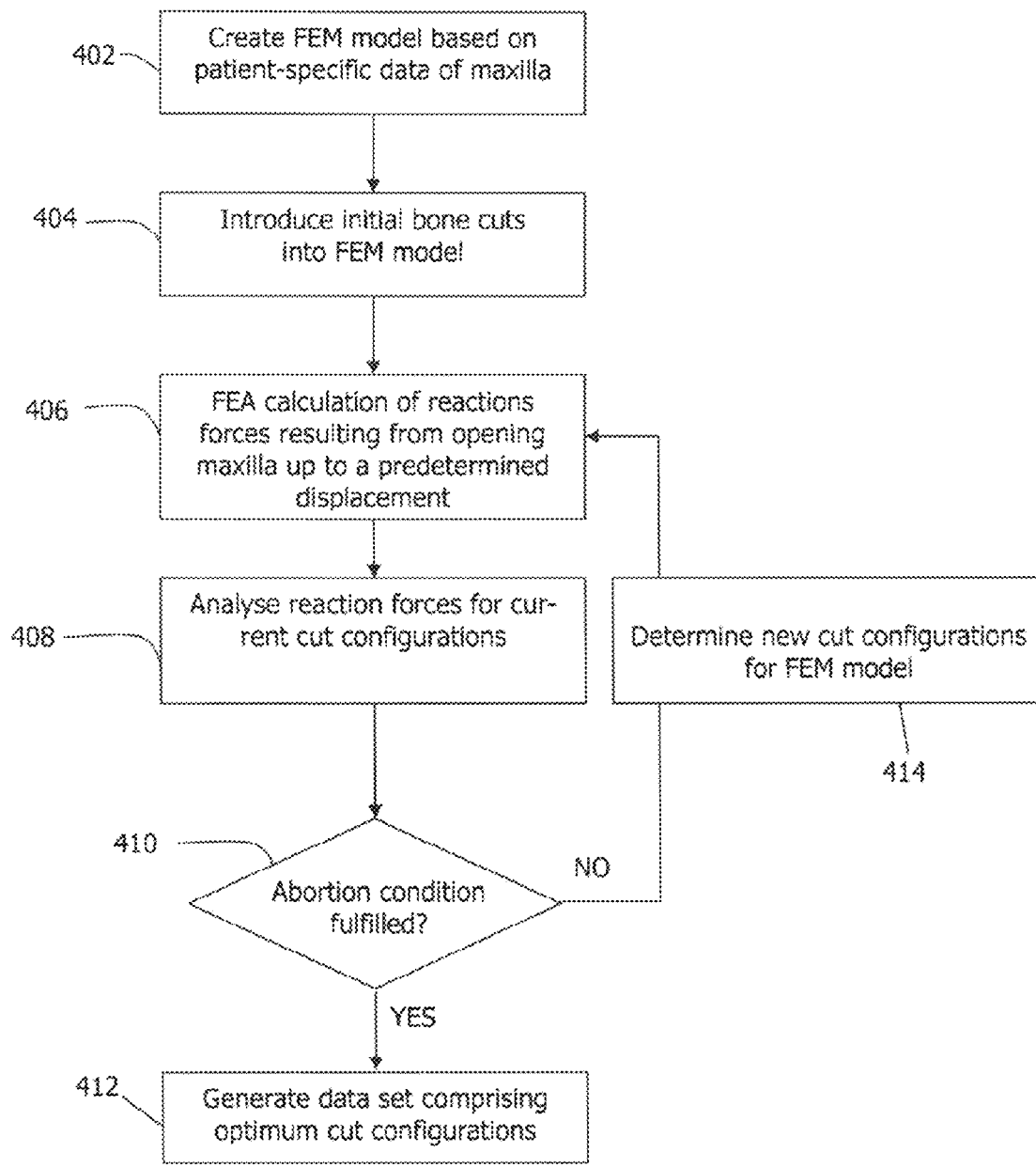
FIG. 4 is a flow diagram illustrating a method embodiment of generating a data set for further surgical use.

FIG. 4 shows a flow diagram 400 that illustrates an embodiment of a computer-implemented method of generating a data set that geometrically defines cut configuration data using the system 100 of FIG. 1. The generation of a data set as illustrated in FIG. 4 will be discussed with reference to the exemplary hardware components shown in FIG. 1 and the accompanying drawings of FIGS. 5 to 12.

In an optional initial step not illustrated in FIG. 4, the computing device 110 obtains patient-specific data of a maxilla 200. The patient-specific data may be received from any one of the internal storage 116, the external storage 130 and the computer network 160. The patient-specific data have been obtained by medical imaging (e.g., using Computer Tomography, Conn., or in any manner) and may be provided in the form of a data file. The patient-specific data may be provided in an STL or Digital Imaging and Communications in Medicine (DICOM) format. In one exemplary variant, the patient-specific data are provided in the form of voxel-based data. It will be appreciated that depending on the nature of the patient-specific data, the patient-specific data may be subjected to dedicated processing operations before or during the process depicted in FIG. 4 (e.g., to convert CT data to surface data in accordance with, for example, the STL standard).

After the patient-specific data have been obtained, in step 402 the processor 114 processes those data to create a numeric model of the maxilla 200. The numeric model thus created is indicative of mechanic properties of the maxilla 200 (e.g., of its stiffness properties). The numeric model may be a mesh-based or a meshless model. As an example of a mesh-based model, a model created by Finite Element Modelling (FEM) will be discussed hereinafter.

Figure 5:
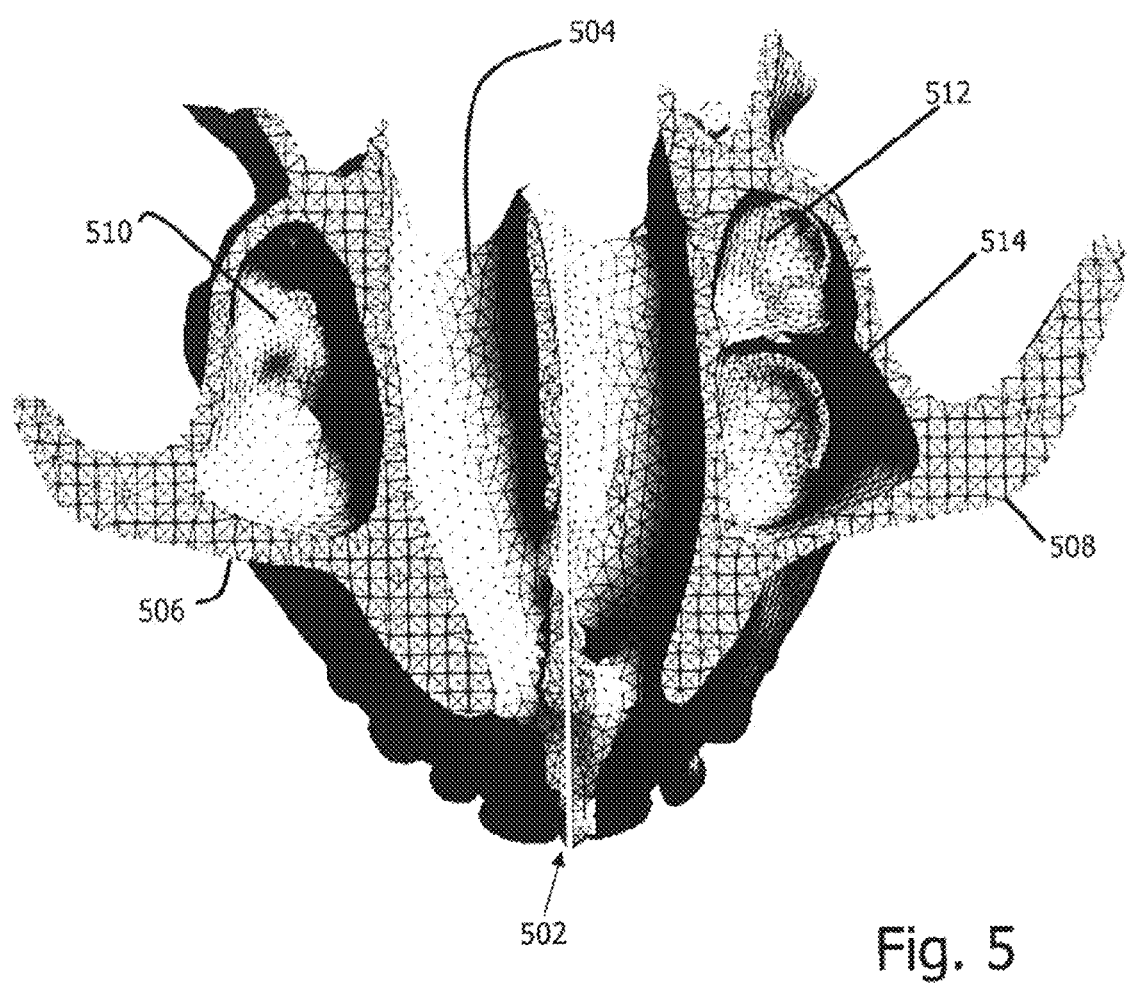
FIG. 5 is a schematic diagram visualizing a numeric FEM model of a patient's maxilla.

The processing operations carried out by the processor 114 in the present embodiment create a three-dimensional numeric FEM model 500 of the maxilla 200 as illustrated in FIG. 5. In FIG. 5, the same anatomic structures as in FIG. 2A can be identified and have been denoted with similar reference numerals.

To generate the FEM model 500, three-dimensional patient-specific DICOM data are initially segmented and transformed into STL data to obtain a voxel-based three-dimensional model of the maxilla 200 (and, optionally, of further portions of the patient's skull). The resulting voxel-based model is then analyzed to determine one or both of three-dimensional contour data and three-dimensional stiffness data for the maxilla 200. The contour data generally describe an outer surface of the maxilla 200, while the stiffness data reflect local stiffness values for the maxilla 200. Both the contour data and the stiffness data may be derived by evaluating grey values associated with the individual voxels. This derivation may comprise threshold decisions to separate bony structures and assess stiffness variations as generally known in the art. The contour data and the stiffness data thus obtained are finally subjected to a Finite Element Analysis (FEA) to calculate the FEM model 500 of FIG. 5 in step 402. Here, each voxel may be mapped onto one finite element.

The FEM model 500, and the numeric model in general, may in one configuration be a static model. Alternatively, the numeric model may take into account visco-elastic properties of the maxilla 200.

In a next step 404 one or more initial bone cuts are introduced into the FEM model 500. It should be noted that in alternative embodiments the bone cuts could have already been introduced into the patient-specific data (e.g., the DICOM or STL data based on which the FEM model 500 is created in step 402).

The initial bone cuts may comprise standard bone cuts (such as the bone cut 502 in the palatine region 504 as illustrated in FIG. 5 and bone cuts in the pterygoid regions). The cut configurations underlying those standard bone cuts may be predefined and automatically introduced by the system 100 in either the patient-specific data (step 402) or, as in the present case, in the FEM model 500. The cut configurations underlying the standard bone cuts need not be changed during the following procedures illustrated in FIG. 4.

Figure 6:
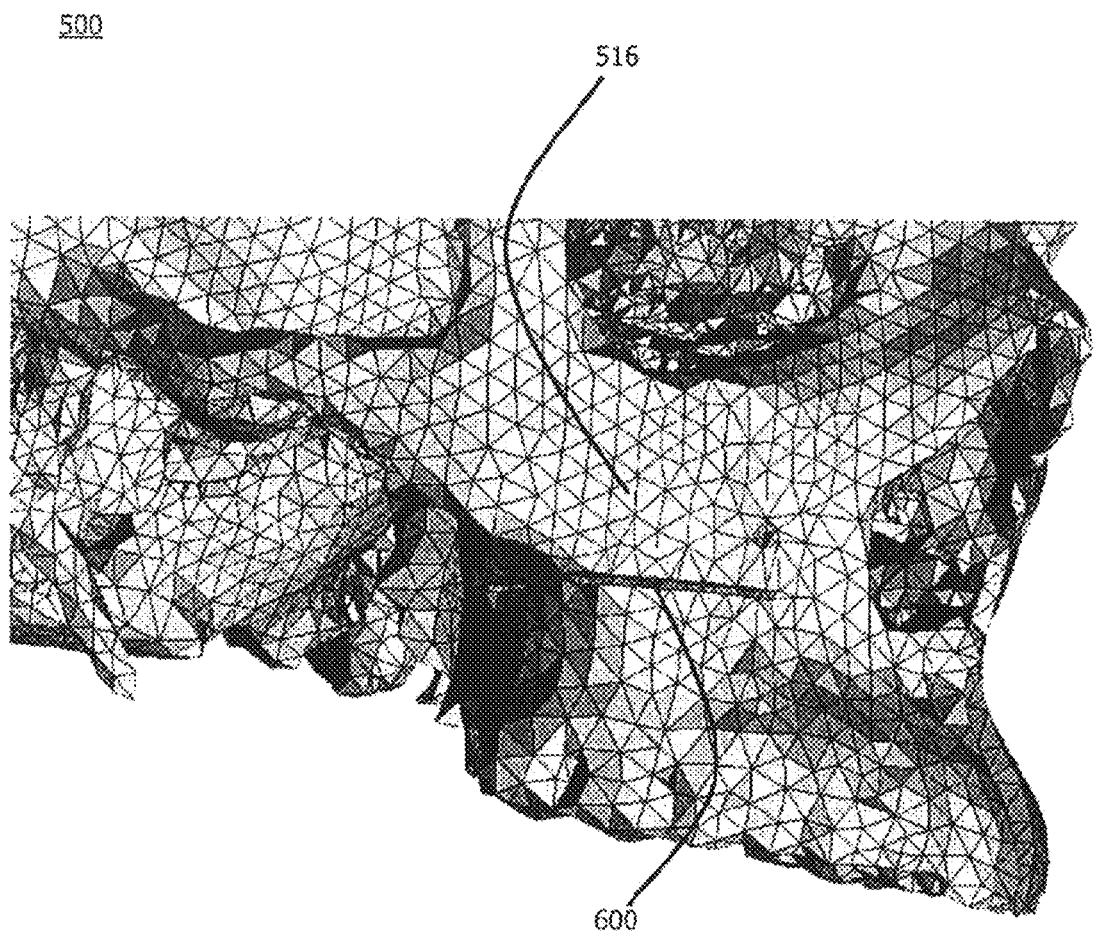
FIG. 6 is a schematic diagram of the FEM model of FIG. 6 with an incorporated bone cut.

In addition to the standard bone cuts, one or more further bone cuts 600 in at least one of the left hand side 506 and the right hand side 508 of the numeric model 500 are introduced as shown in FIG. 6. In the present case it will be assumed that one such bone cut 600 is provided in a lateral midface area 516 in each of the left hand side 506 and the right hand side 508 of the numeric model 500. The number of bone buts 600 as well as an initial cut configuration for each bone cut 600 may be pre-defined by the system 100 or by a user operating the system 100.

For each bone cut 502, 600 the associated cut configuration comprises geometric data defining the position and length of the bone cut 502, 600. As an example, the bone cut 600 may be represented in the numeric model 500 as a linear (curved or straight) boneless structure having two boundary points and a width. The two boundary points and the width may be indicated in a coordinate system of the FEM model 500. As will be appreciated, the coordinates of the two boundary points of the bone cut 600 in the FEM model 500 will also define the cut length for a straight bone cut. A curved bone cut 600 may be defined by a spline additionally comprising intermediate points.

After all initial cuts 502, 600 have been introduced into the FEM model 500 in step 404, the reaction forces necessary to open the maxilla up to a predetermined displacement (e.g., as defined by the system 100 or a user operating the system 100) are calculated in step 406. As an example, the predetermined total displacement may be set to a value between 2 and 16 mm (e.g., between 6 to 14 mm). In the case the FEM model 500 is indicative of visco-elastic properties of the maxilla 200, the predetermined displacement (or predetermined distraction force) may be applied in multiple, temporarily spaced apart steps so as to allow for a setting after each step.

The calculation in step 406 is based on FEA and iteratively repeated. In this regard, the cut configurations initially provided for the bone cuts 600 (i.e., the bone cuts provided to compensate for stiffness variations) are iteratively optimized. The cut configurations may be repeatedly changed (e.g., within a predefined parameter corridor) until optimum cut configurations have been obtained. As will be appreciated, optimum cut configurations balance the asymmetry of the maxilla 200 in stiffness (and the asymmetric reaction forces or asymmetric displacements upon distraction).

Figure 7:
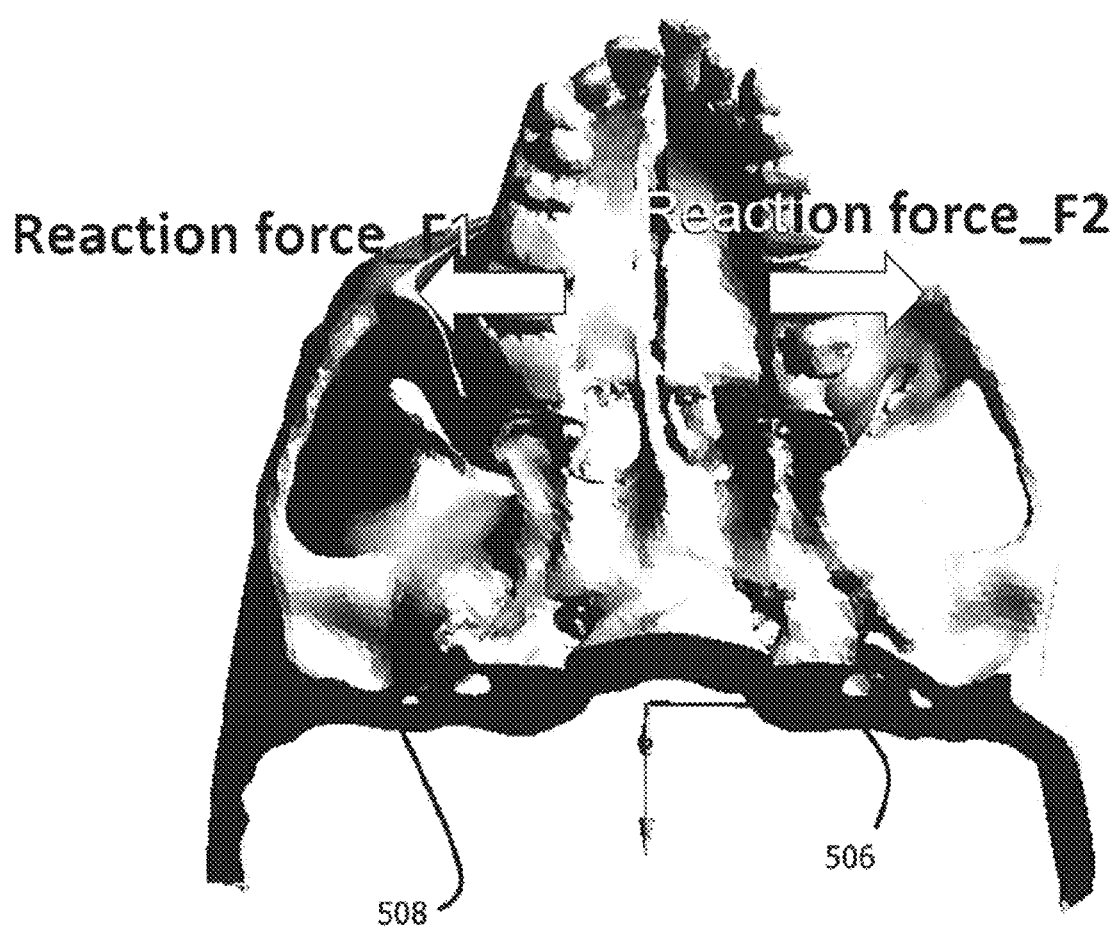
FIG. 7 is a schematic diagram illustrating distraction forces as applied or as derived from the FEM model of FIG. 5.

In the present case the numeric model 500 is iteratively optimized with respect to the cut configurations underlying the bone cuts 600 until, for the predetermined displacement, approximately the same amounts of reaction forces F1, F2 are visualized to open up the maxilla 200 as illustrated for the associated FEM model 500 in FIG. 7. In the FEM model 500 of FIG. 7, the reaction forces F1, F2 are visualized in the form of two opposite force vectors rooted in the first molars or the canines on the left hand side 506 and the right hand side 508 of the FEM model 500, respectively. In other embodiments, four force vectors may be used that root in the first molars and the canines on each of the left hand side 506 and the right hand side 508 of the numeric model 500. In general, the force or displacement vectors may root in places where the distractor device will be applied to the patient.

In step 408 the resulting amounts of the reaction forces F1, F2 (and, optionally, other the optimization parameters) for the predetermined displacement are analyzed with respect to the current cut configurations. If both reaction forces F1, F2 have approximately the same amount (and, optionally, if further conditions hold), it will be recognized in step 410 that an abortion condition is fulfilled as the current bone cut configurations (and the associated bone cuts 600) will lead to symmetric distraction properties. From step 410 the method then proceeds to step 412 to generate a data set comprising the optimum cut configurations. This data set may be processed as will be described below in more detail.

If, on the other hand, it should be determined in step 410 that the abortion condition is not yet fulfilled, for at least one of the bone cuts 600 a new cut configuration is determined in step 414 and the method loops back to step 406 for the next iteration.

Figure 8:
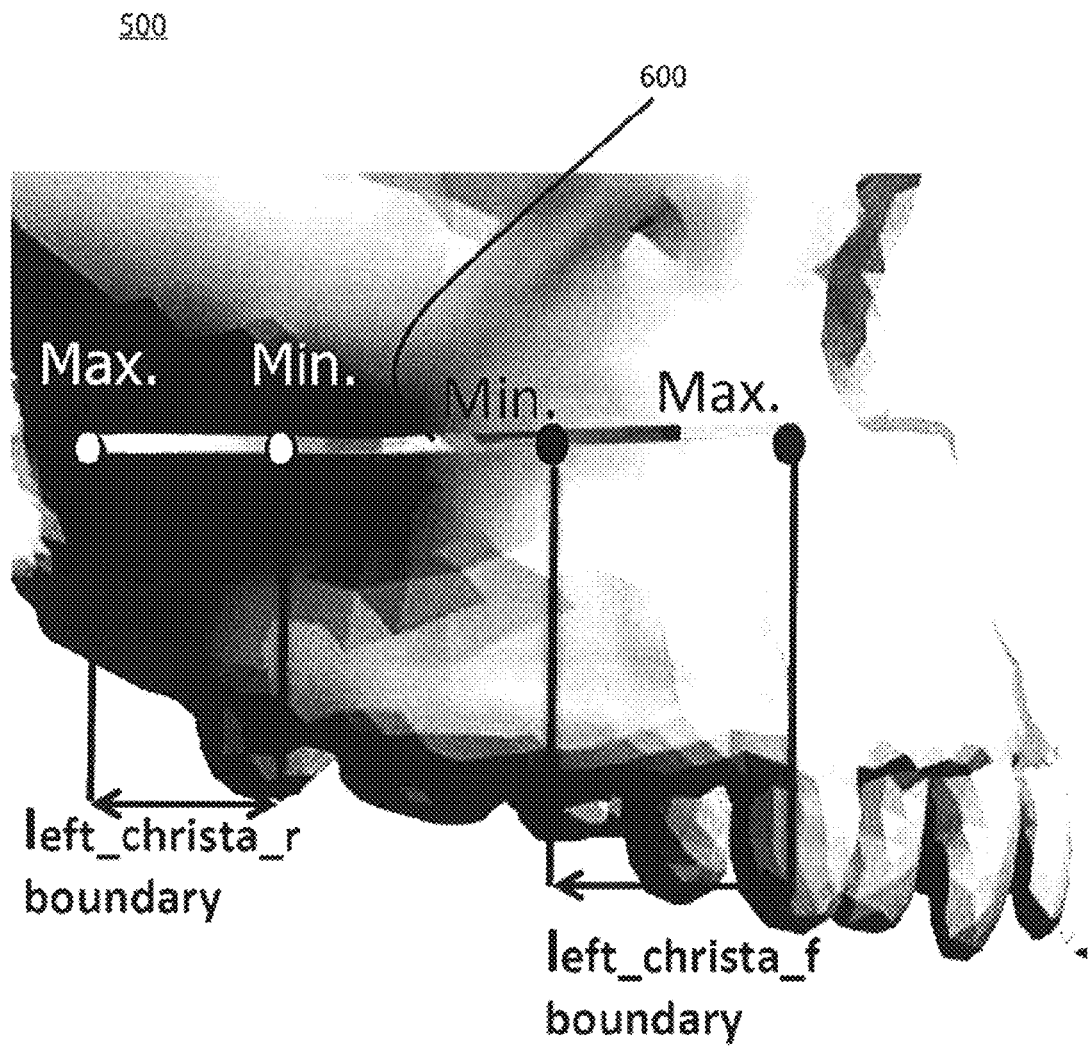
FIG. 8 is a schematic diagram illustrating the process of iteratively determining bone cut boundary points based on the FEM model of FIG. 5.

The initial position and shape of a cutting line (e.g., a spline) underlying each bone cut 600 may have been predefined by the system 100 or a user operating the system 100. In the present embodiment it will be assumed that positions of the two boundary points of the associated bone cut 600 and, optionally, of intermediate points that define the shape of the cutting line are iteratively optimized. For such an iterative optimization, the position of the boundary points of each bone cut 600 may be varied within a predefined parameter range between a maximum value and a minimum value as illustrated in FIG. 8. Accordingly, the new cut configurations are determined in step 414 by shifting the boundary points of each bone cut 600 within those predefined boundary regions. It will be appreciated that in other embodiments the positions of intermediate points may be optimized only (e.g., the boundary points for each bone cut 600 may remain fix) or in addition to the boundary points.

In the embodiment discussed above, it has been assumed that the abortion condition is defined by equalizing, or balancing, the amount of the opposite reaction forces resulting from a predefined displacement for each of the left hand side 506 and the right hand side 508 of the numeric model 500. In other embodiments, the displacements on each of the left hand side 506 and the right hand side 508 of the numeric model 500 may be equalized, or balanced, for opposite distraction forces of a predefined amount. It will further be appreciated that in other embodiments a more complex optimization procedure may be performed that takes into account one or more additional or alternative optimization parameters. In this regard, FIG. 9 shows a table 900 that illustrates an optimization criterion that optimizes a weighted combination of minimum cut lengths, minimum reaction forces and reaction force symmetry. In the embodiment of FIG. 9, reaction force symmetry (i.e., equalization of the amounts of the reaction forces F1 and F2) is associated with the highest weight (weighting factor 5), the reduction of the sum of the amounts of the distraction forces F1, F2 is given the second highest weight (weighting factor 3) and the cutting length minimization for each of the two bone cuts 600 is given the lowest weight (weighting factor 1).

Figure 10:
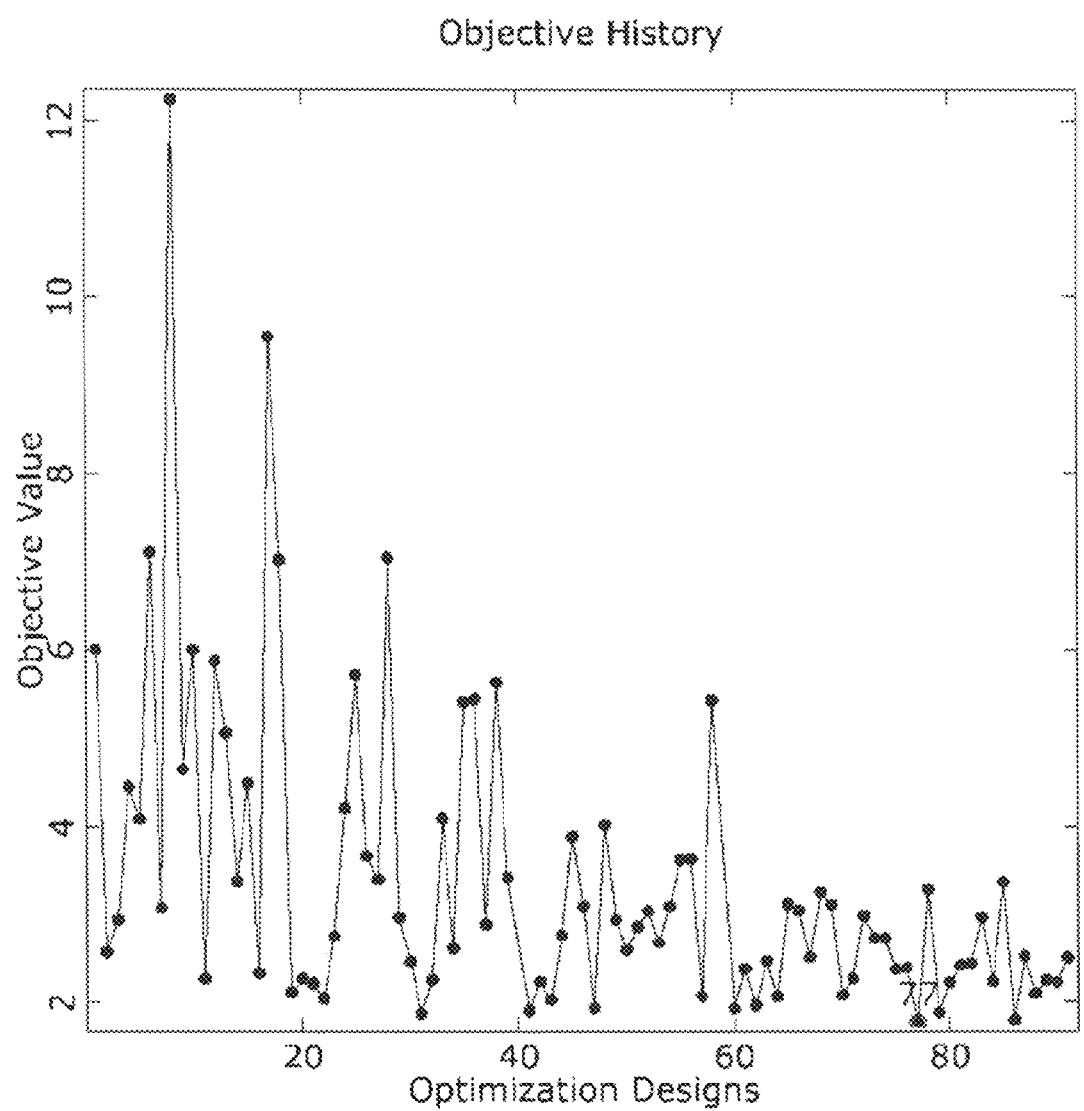
FIG. 10 is a schematic diagram illustrating a variability of the optimization criterion of FIG. 9 during an iterative optimization procedure.

The positions of the boundary points of the bone cuts 600 are iteratively varied so as to minimize the mathematical expression in the last line of table 900. FIG. 10 illustrates in a diagram 1000 the underlying optimization procedure. As can be gathered from the diagram 1000 of FIG. 10, the cut configuration underlying a specific design (i.e., specific boundary point positions) 77 minimize the expression illustrated in FIG. 9. The same information can be derived from the schematic diagram 1100 of FIG. 11, which illustrates the substantial decrease of the difference between the opposite reaction forces from design 1 via design 47 to design 77, while at the same time the sum of the amounts of the reaction forces F1, F2 is reduced slightly and while obtaining optimum cut lengths that lie between the minimum cut length and the maximum cut length as illustrated in FIG. 8.

It will be appreciated that the various optimization parameters illustrated in FIG. 9 can also be used individually or can be combined otherwise as needed depending on the mechanical conditions and requirements. It will also be appreciated that while in the present embodiment the minimization of an optimization criterion has exemplarily been described to underline the abortion condition illustrated in step 410 of FIG. 4, in other embodiments a maximization of a different optimization criterion may be employed.

Further, it will be appreciated that the present technique is not restricted to an iterative procedure based on one or more optimization parameters. Rather, it will also be possible to initially define multiple cut configurations (i.e., for each of multiple bone cuts) and to then test predefined permutations or parameter ranges of such cut configurations and analyze each permutation or parameter set with respect to one or more quality parameters. In one implementation, the permutations or parameter ranges are derived based on different predefined boundary point positions (see FIG. 8). The quality parameters may include one or more of the parameters illustrated in table 900 of FIG. 9. After all or a predefined number of cut configuration permutations or parameter sets have been analyzed, the particular configuration associated with the highest quality criterion may be selected for generating the data set intended for further use.

As mentioned above, the method embodiment illustrated in FIG. 4, or an alternative method embodiment, results in a data set comprising cut configurations for the actual surgical procedure. The data set may, for example, define for each bone cut 600 two optimum boundary points (and, optionally, a width) in a coordinate system of the FEM model 500. In a typical case, the data set 1200 will comprise an individual cut configuration for a first bone cut 600 on the left hand side 506 of the numeric model 500 as well as for a second bone cut 600' on the right hand side 508 as visualized in FIG. 12.

Figure 12:
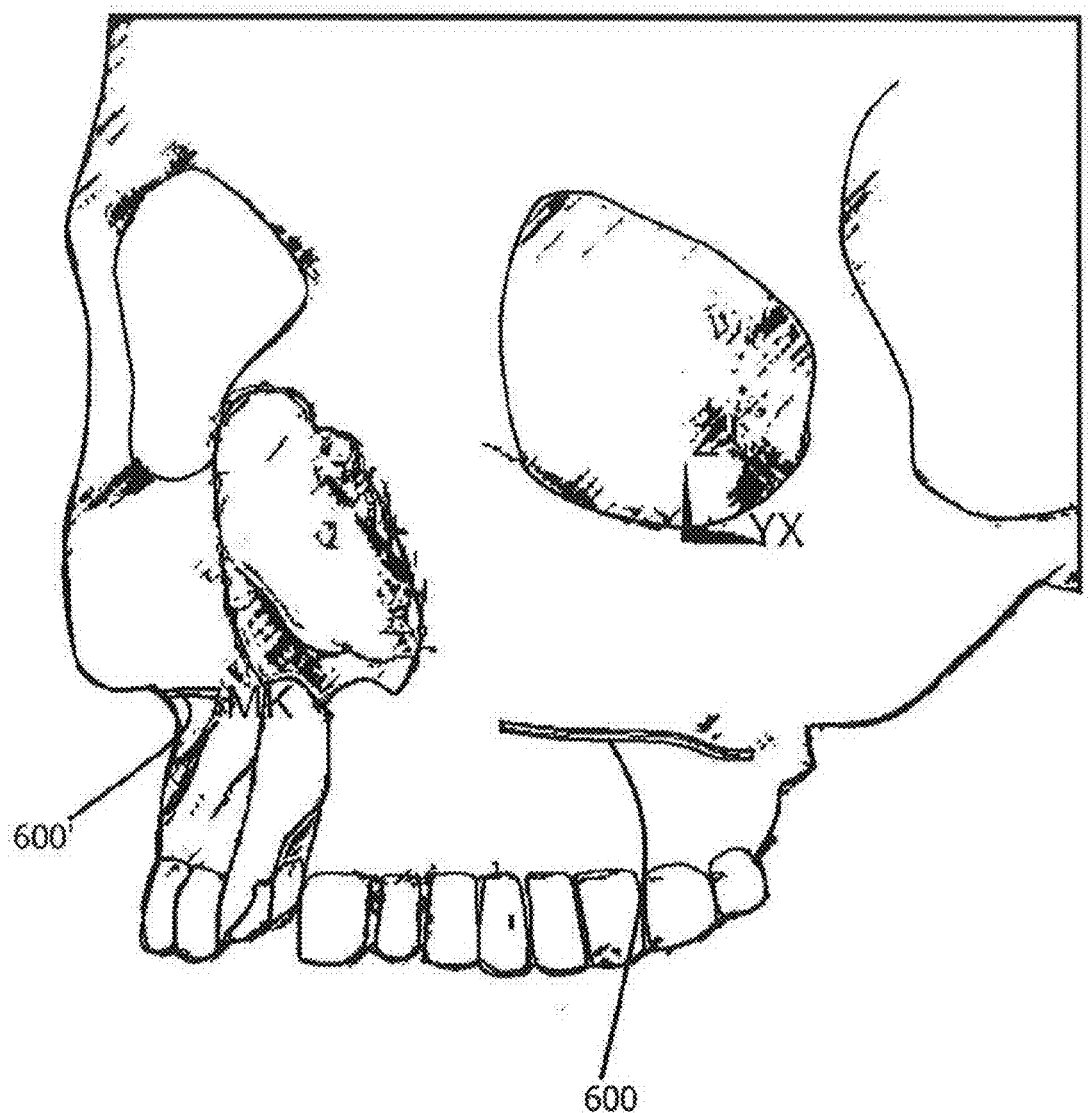
FIG. 12 is a schematic diagram visualizing a data set comprising a cut configuration obtained by the optimization procedure of FIG. 10.

The data set 1200 shown in FIG. 12 has been derived from the FEM model 500 and includes the bone cuts 600, 600' with respectively optimized boundary positions. In the data set 1200, the bone cuts 600, 600' may be incorporated as boneless structure (e.g. voids).

Figure 13:
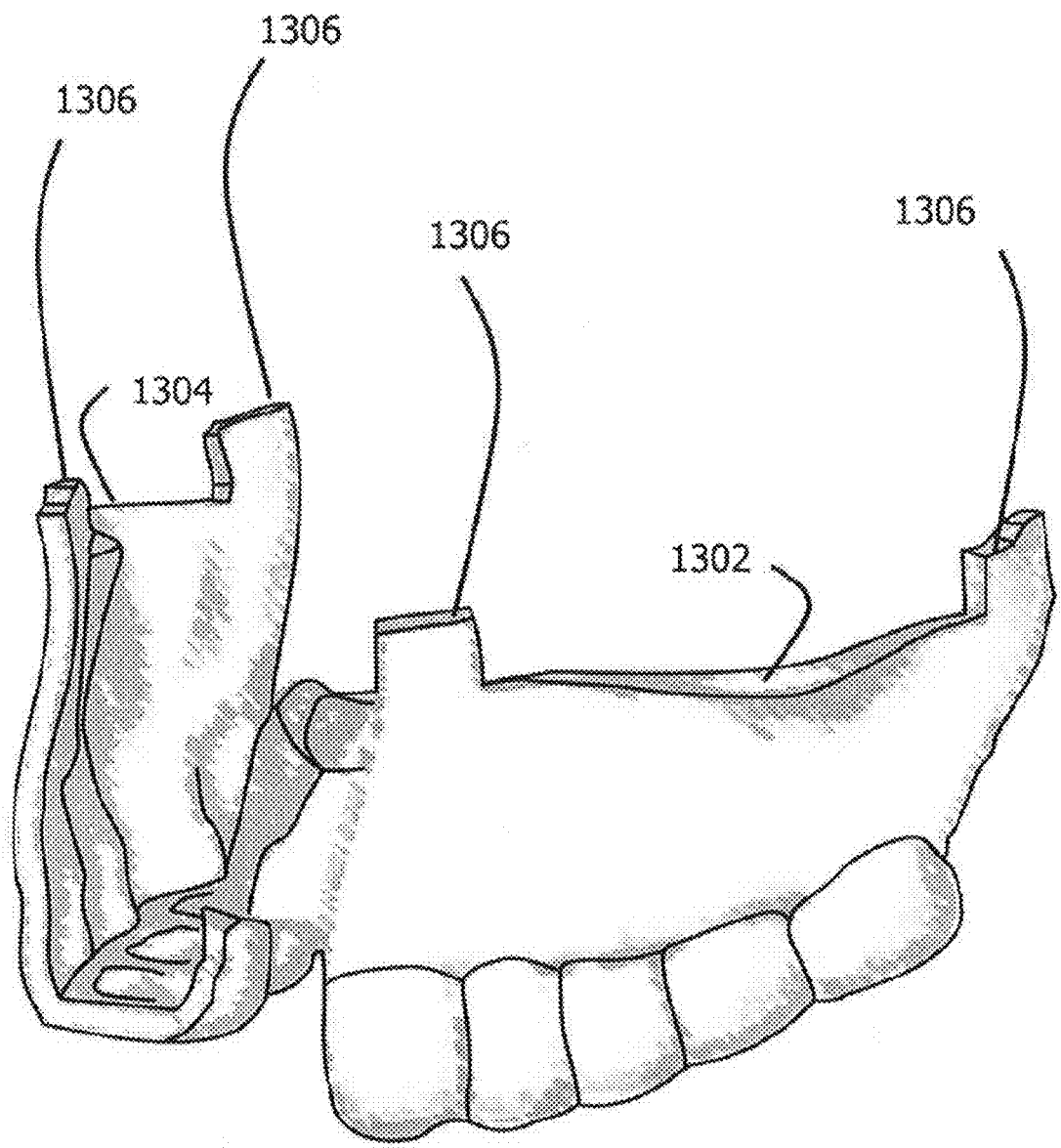
FIG. 13 is a schematic diagram illustrating an embodiment of a surgical template for bone cutting derived from the data set visualized in FIG. 12.
Figure 14:
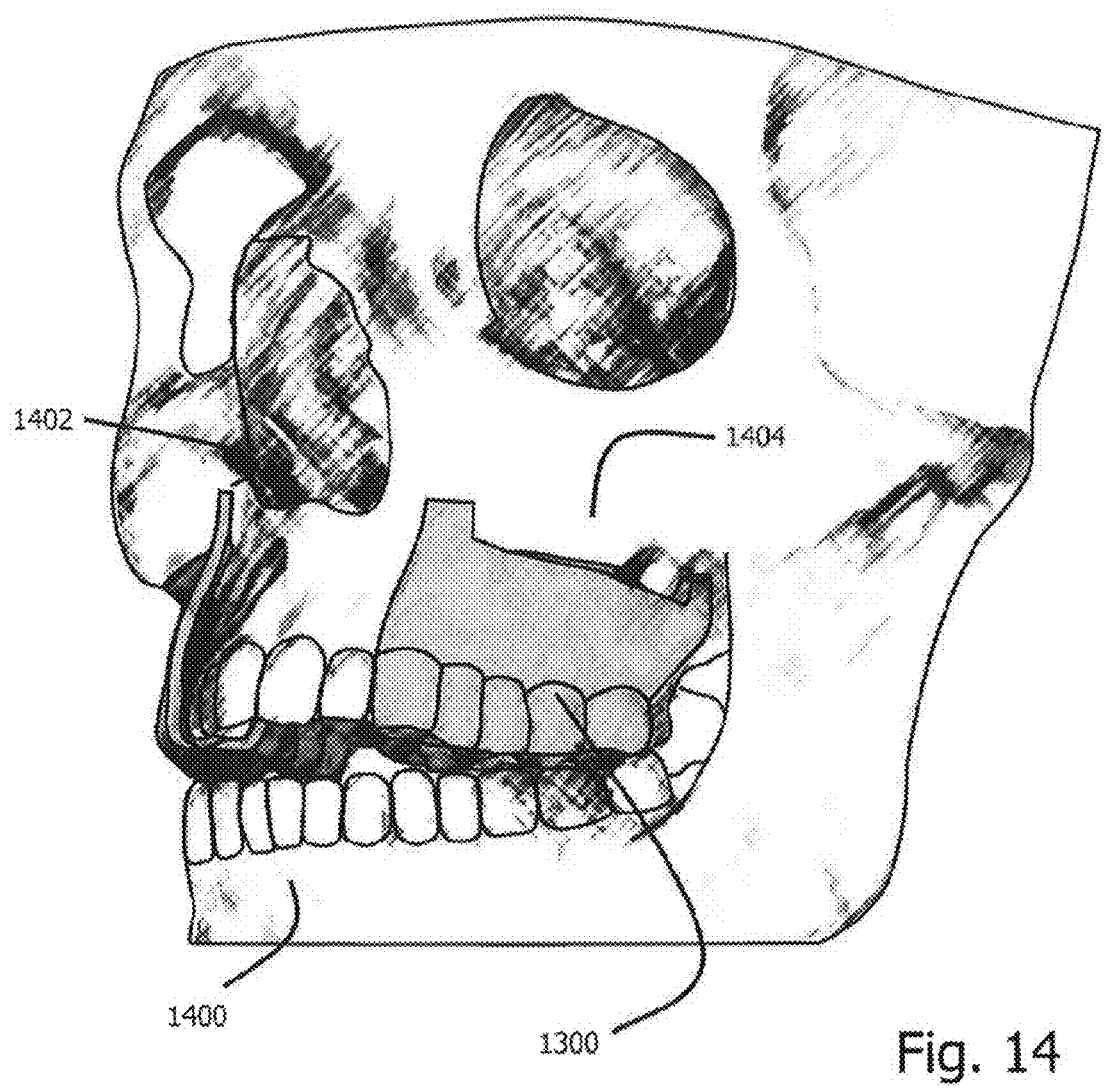
FIG. 14 is a schematic diagram illustrating the positioning of the surgical template of FIG. 13 relative to a patient's skull.

In one implementation, the resulting data set 1200 is a _STL data set and fed to the manufacturing device 140 (e.g., a rapid prototyping device) illustrated in FIG. 1. Based on that data set 1200, and optionally further data derived, for example, from the numeric model 500, the manufacturing device 140 manufactures a surgical template or jig for bone cutting. FIG. 13 illustrates an embodiment of such a surgical template 1300, and FIG. 14 visualizes how that template 1300 will be applied to a skull 1400 of the patient to define the locations 1402, 1404 where a surgical saw is to be applied. The template 1300 comprises two surfaces 1302, 1304 reflecting the cut configurations for the bone cuts 600, 600'. The surfaces 1302, 1304 are limited by corresponding boundary structures 1306 reflecting the boundary points that were derived based on the numeric model (see FIG. 8).

It will be appreciated that the data set obtained in step 412 may be processed further for the purpose of controlling the manufacturing device 140 as needed. As an example, the tips of the teeth may be trimmed away so as to obtain an optimized seating of the surgical template 1300 at the maxilla 200. Additionally, a user of the system 100 may have the possibility to optimize the surgical template 1300 as needed.

It will also be appreciated that the use of the data set 1200 generated in step 412 is not limited to the generation of a surgical template 1300 or jig for bone cutting. Rather, the corresponding data set 1200 may also be used to control a computer-assisted surgery system. As an example, such a surgery system may comprise a robotic arm to which a bone saw is attached. The actual cutting operation performed by the robotic arm is controlled in accordance with the optimum cut configurations as represented in the data set 1200.

In another implementation, the data set 1200 may be used for the purpose of a surgical navigation system. Such navigation systems typically track a position of a surgical tool, such as a surgical saw, relative to a patient. The corresponding tracking data are then visualized on a display device relative to a pre-operative or intra-operative image of the patient's maxilla 200. That image may be enhanced a with a representation the optimum cut configurations so as to visualize to the surgeon the current position of the surgical saw (as determined by tracking) relative to the position where the bone cuts 600 are to be made (as determined for the data set 1200).

As has become apparent from the above description, the technique presented herein may in many ways assist the surgeon in transverse maxillary distraction. The resulting assistance leads to an improved surgical result with respect to skeletal symmetry at the end of the distraction procedure.

In the foregoing principles, embodiments and various modes of implementing the technique disclosed herein have exemplarily been described. The present invention should not be construed as being limited to the particular principles, embodiments and mode discussed herein. Rather, it will be appreciated that various changes and modifications may be made by a person skilled in the art without departing from the scope of the present invention as defined in the claims that follow.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A computer-implemented method of generating a data set that geometrically defines at least one bone cut configuration for transverse maxillary distraction, the method comprising:

creating, based on patient-specific data of a maxilla, a numeric model representative of mechanic properties of the maxilla;

determining, based on the numeric model thus generated, one or more cut configurations for one or more first bone cuts on at least one of a left hand side and a right hand side of the maxilla, wherein the one or more cut configurations are determined so as to compensate for asymmetric mechanic properties of the maxilla upon distraction; and generating a data set indicative of the one or more cut configurations.

2. The method of claim 1, wherein the one or more first bone cuts are defined to at least partially extend in a lateral midfacial area.

3. The method of claim 1, wherein each cut configuration comprises data indicative of at least one of a cutting plane, a cutting line, a cutting direction, a cutting length and at least one bone cut boundary point.

4. The method of claim 1, wherein determining the one or more cut configurations comprises introducing the one or more first bone cuts in the numeric model and analyzing the resulting numeric model as to its mechanic properties upon distraction.

5. The method of claim 1, wherein determining the one or more cut configurations comprises introducing one or more second bone cuts in the numeric model and analyzing the resulting numeric model as to its mechanic properties upon distraction, wherein the one or more second bone cuts at least partially separate in the numeric model regions moved apart upon distraction from regions essentially not affected by distraction.

6. The method of claim 1, wherein creating the numeric model comprises:
processing the patient specific data to determine at least one of contour data and stiffness data for the maxilla; and calculating the numeric model from at least one of the contour data and the stiffness data.

7. The method of claim 1, wherein the numeric model is indicative of at least one of a stiffness of the maxilla, a reaction force upon distraction of the maxilla and a displacement upon distraction of the maxilla.

8. The method of claim 1, wherein the one or more cut configurations are determined, based on the numeric model, so as to balance at least one of a stiffness asymmetry of the maxilla, asymmetric reaction forces upon distraction and asymmetric displacements upon distraction.

9. The method of claim 1, wherein determining the one or more cut configurations comprises one of:
applying a distraction force on each of a first side and a second side of the numeric model that correspond to the left hand side and the right hand side of the maxilla, respectively, and determining the resulting displacements of the first side and the second side of the numeric model, respectively; and
applying a displacement on each of the first side and the second side of the of the numeric model and determining the resulting reaction forces on the first side and the second side of the numeric model, respectively.

10. The method of claim 9, wherein the distraction forces or displacements are applied in at least one of a region of the molars and a region of the canines.

11. The method of claim 1, wherein determining the one or more cut configurations based on the numeric model comprises applying an iterative calculation procedure based on one or more optimization parameters.

12. The method of claim 11, wherein in each iteration at least one new cut configuration is calculated and a new numeric model is created based thereon for the next iteration.

13. The method of claim 11, wherein the one or more optimization parameters include at least one of a minimum cut length, equalization of stiffnesses on a first side and a second side of the numeric model that correspond to the left hand side and the right hand side of the maxilla, respectively, equalization of displacements on the first side and the second side, equalization of distraction or reaction forces on the first side and the second side, and minimum distraction or reaction forces.

14. The method of claim 1, wherein initially multiple cut configurations are defined for which associated numeric models are determined and analyzed as to one or more quality parameters.

15. The method of claim 14, wherein the one or more quality parameters include at least one of a minimum cut length, equalization of stiffnesses on a first side and a second side of the of the numeric model that correspond to the left hand side and the right hand side of the maxilla, respectively, equalization of displacements on the first side and the second side, equalization of distraction or reaction forces on the first side and the second side, and minimum distraction or reaction forces.

16. A computer program comprising: program code portions for performing the steps of claim 1 when the computer program is executed by a computing device.

17. The computer program of claim 16, stored on a computer readable recording medium.

18. The method of claim 1, wherein the data set generated is for at least one of manufacturing a surgical template or jig for bone cutting, controlling a computer-assisted surgery system for bone cutting and controlling a surgical navigation system for bone cutting.

19. A surgical template or jig for bone cutting, manufactured on the basis of the data set generated according to claim 1.

20. A computer-assisted surgery system, controlled on the basis of the data set generated according to claim 1.

21. A surgical navigation system, controlled on the basis of the data set generated according to claim 1.

22. A computer-implemented method of generating a data set that geometrically defines at least one bone cut configuration for transverse maxillary distraction, the method comprising:
creating, based on patient-specific data of a maxilla, a numeric model representative of mechanic properties of the maxilla;
determining, based on the numeric model thus generated, one or more cut configurations for one or more first bone cuts on at least one of a left hand side and a right hand side of the maxilla, wherein the one or more cut configurations are determined so as to compensate for asymmetric mechanic properties of the maxilla upon performing the transverse maxillary distraction, and wherein determining the one or more cut configurations comprises introducing the one or more first bone cuts in the numeric model, analyzing the resulting numeric model as to its mechanic properties upon distraction, and applying an iterative calculation procedure based on one or more optimization parameters, wherein, in each iteration, at least one new cut configuration is calculated, and a new numeric model is created based thereon for the next iteration; and
generating a data set indicative of the one or more cut configurations.

* * * * *